United States Patent
Eblacas et al.

(10) Patent No.: US 9,387,097 B2
(45) Date of Patent: Jul. 12, 2016

(54) IMPLANT ASSEMBLY WITH TACTILE INDICATOR

(71) Applicant: W. L. Gore & Associates, Inc., Newark, DE (US)

(72) Inventors: Julio E. Eblacas, Milpitas, CA (US); Linda N. Elkins, Redwood City, CA (US); William P. Witort, Berkeley, CA (US)

(73) Assignee: W. L. Gore & Associates, Inc., Newark, DE (US)

( * ) Notice: Subject to any disclaimer, the term of this patent is extended or adjusted under 35 U.S.C. 154(b) by 543 days.

(21) Appl. No.: 13/675,557

(22) Filed: Nov. 13, 2012

(65) Prior Publication Data

US 2013/0123900 A1    May 16, 2013

Related U.S. Application Data (60) Provisional application No. 61/560,720, filed on Nov. 16, 2011.

(51) Int. Cl.
| *A61F 2/06* | (2013.01) |
|---|---|
| *A61F 2/82* | (2013.01) |

(Continued)

(52) U.S. Cl.
CPC ... *A61F 2/82* (2013.01); *A61F 2/95* (2013.01); *A61F 2/954* (2013.01); *A61F 2/97* (2013.01); *A61F 2/07* (2013.01); *A61F 2/856* (2013.01); *A61F 2002/9511* (2013.01)

(58) Field of Classification Search
CPC ............... A61F 2002/9511; A61F 2002/9505; A61F 2/95; A61F 2/954; A61F 2/97; A61F 2/966; A61F 2/962; A61F 2002/011; A61F 2002/9522; A61F 2002/9583; A61F 2002/9586; A61F 2002/9665; A61F 2/2427; A61F 2/2436; A61F 2/243; A61F 2/2433; A61F 2/2439; A61F 2/958
USPC ........................... 623/1.11, 1.23, 12; 606/198
See application file for complete search history.

(56) References Cited

U.S. PATENT DOCUMENTS

| 6,015,431 A * | 1/2000 | Thornton et al. ............ 623/1.14 |
|---|---|---|
| 6,352,561 B1 * | 3/2002 | Leopold et al. .............. 623/1.23 |

(Continued)

FOREIGN PATENT DOCUMENTS

| CN | 101450019 | 6/2009 |
|---|---|---|
| FR | 2688688 | 9/1993 |

(Continued)

OTHER PUBLICATIONS

International Search Report and Written Opinion for PCT/US2012/065042 mailed Feb. 12, 2003, corresponding to U.S. Appl. No. 13/675,557.

*Primary Examiner* — Jonathan W Miles
*Assistant Examiner* — Erich Herbermann (57) ABSTRACT

The present disclosure describes an assembly comprising an expandable device, a restraining member wrapped circumferentially around the device, a coupling member releasably securing the restraining member, and at least one tactile indicator located on the assembly at a desired point of partial deployment, along with a method for partially deploying the expandable device in a patient. During partial deployment of the expandable device, the coupling member is tensioned and displaced from outside the patient by a clinician, and upon reaching the tactile indicator, a change in tension on the coupling member is felt my the clinician performing the procedure.

22 Claims, 10 Drawing Sheets

(51) Int. Cl.
*A61F 2/95* (2013.01)
*A61F 2/954* (2013.01)
*A61F 2/97* (2013.01)
*A61F 2/07* (2013.01)
*A61F 2/856* (2013.01)

(56) References Cited

U.S. PATENT DOCUMENTS

| | | |
|---|---|---|
| 6,551,350 B1 | 4/2003 | Thornton et al. |
| 6,984,242 B2 | 1/2006 | Campbell et al. |
| 2004/0122503 A1 | 6/2004 | Campbell et al. |
| 2009/0182268 A1 | 7/2009 | Thielen et al. |
| 2012/0022630 A1* | 1/2012 | Wubbeling .................. 623/1.11 |

FOREIGN PATENT DOCUMENTS

| | | |
|---|---|---|
| WO | 93/17636 | 9/1993 |
| WO | 98/27894 | 7/1998 |
| WO | 2006/015323 | 2/2006 |

\* cited by examiner

IMPLANT ASSEMBLY WITH TACTILE INDICATOR

CROSS-REFERENCE TO RELATED APPLICATIONS

This application claims priority to U.S. Provisional Application No. 61/560,720, entitled "ILIAC BIFURCATED ENDOPROSTHESIS MEDICAL APPARATUS AND METHOD OF DEPLOYING SAME" filed on Nov. 16, 2011, which is hereby incorporated by reference in its entirety.

FIELD

The present disclosure relates generally to the delivery and remote stepwise deployment of implantable medical devices.

BACKGROUND

Medical devices are frequently used to treat the anatomy of patients. Such devices can be permanently or semi-permanently implanted in the anatomy to provide treatment to the patient. Frequently, these devices, including stents, grafts, stent-grafts, filters, valves, occluders, markers, mapping devices, therapeutic agent delivery devices, prostheses, pumps, bandages, and other endoluminal and implantable devices, are inserted into the body at an insertion point and deployed to a treatment area using a catheter. Common types of expandable devices include stents and stent-grafts.

Expandable devices such as stents or stent-grafts are used in a variety of places in the human body to repair aneurysms and to support various anatomical lumens, such as blood vessels, respiratory ducts, gastrointestinal ducts, and the like. Expandable devices may have a reduced diameter when in a collapsed configuration, which can be expanded once located at the treatment site in the patient. Expandable devices may be constrained in the collapsed configuration to facilitate transport to the treatment site.

Although moving a medical device to a treatment area and deploying it for a localized medical treatment are common procedures today, fluoroscopy or other imaging techniques are typically needed to track the movement of the device to the treatment site and to track the progress of the deployment once located. One such example of imaging is X-ray fluoroscopy, which is used for real time imaging during the locating and deploying procedures. Although X-ray fluoroscopy provides excellent resolution, it has various practical limitations.

Therefore, new medical devices, systems and methods that allow real time indication of the progress of their deployment are desirable.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure, wherein.

DETAILED DESCRIPTION OF THE ILLUSTRATED EMBODIMENTS

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting.

With that said, and as will be described in more detail herein, various embodiments of the present disclosure generally comprise medical assemblies configured for partial deployment of a medical device in a patient in stages. In this regard, at least one tactile indicator configured on the assembly relays an indication of the stage of deployment to the clinician. For example, a medical device in accordance with the present disclosure may be deployed in stages that are tracked in real time by tactile events sensed by the clinician.

As used herein, "proximal" indicates a position closer to a practitioner, while "distal" indicates a position further from a practitioner.

As used herein, "medical devices" can include, for example, stents, grafts, stent-grafts, filters, valves, occluders, markers, mapping devices, therapeutic agent delivery devices, prostheses, pumps, bandages, and other endoluminal and implantable devices that are implanted, acutely or chronically, in the vasculature (vessel) or other body lumen or cavity at a treatment region or site. Such medical devices can comprise a flexible material that can provide a fluid-resistant or fluid-proof surface, such as a vessel bypass or blood occlusion.

As used herein, an "expandable implant" can include, for example, any medical device suitable for delivery to the treatment site at a delivery diameter and capable of dilation from the diameter of the delivery profile, through a range of intermediary diameters, up to a maximal, pre-determined functional diameter. Such expandable devices may include, for example, stents, grafts, and stent-grafts.

In various embodiments, an expandable implant may comprise a radially collapsed configuration suitable for delivery to the treatment area of the vasculature of a patient. Such an expandable implant may be constrained in a radially collapsed configuration and mounted onto a delivery device such as catheter. The diameter of the expandable implant in the collapsed configuration is preferably small enough for the implant to be delivered through the vasculature to the treatment area. In various embodiments, the diameter of the collapsed configuration is small enough to minimize the crossing profile of catheter and reduce tissue damage to the patient. In the collapsed configuration, the expandable implant may be guided through the vasculature.

In various embodiments, an expandable implant may comprise a radially expanded configuration suitable for implanting the device in the treatment area of a patient's vasculature. In the expanded configuration, the diameter of an expandable implant may be approximately the same as the vessel to be repaired. In other embodiments, the diameter of expandable implant in the expanded configuration may be slightly larger than the vessel to be treated to provide a traction fit within the vessel.

In various embodiments, an expandable implant may comprise a self-expandable device, such as a self-expandable stent-graft. Such devices dilate from a radially collapsed configuration to a radially expanded configuration when unconstrained. As used herein, the term "constrain" may mean (i) to limit expansion, occurring either through self-expansion or expansion assisted by a device, of the diameter of an expandable implant, or (ii) to cover or surround, but not otherwise restrain, an expandable implant (e.g., for storage or biocompatibility reasons and/or to provide protection to the expandable implant and/or the vasculature).

In various embodiments, an expandable implant may comprise a device that is expanded with the assistance of a secondary device such as, for example, a balloon.

In various embodiments, an expandable implant may comprise a stent-graft. Stent-grafts are designed and generally comprise one or more stent components that form a support structure or scaffold, with one or more graft members displaced over and/or under the stent.

In various embodiments, the support structure may comprise, for example, a plurality of stent rings, cut tubes, wound wires (or ribbons) or flat patterned sheets rolled into a tubular form. Stent rings may be operatively coupled to one another with a wire. A wire used to couple stent rings may attach to the peak of a first stent ring and a valley of a second stent ring. The stent ring may be arranged such that the peaks in valleys are in-phase (e.g., the peaks first stent ring share a common centerline with the peaks of the second stent) or out of phase (e.g., the peaks of the first stent ring share a common centerline with the valleys of the second stent ring).

Stent components for support structure can be formed from metallic, polymeric or natural materials and can comprise conventional medical grade materials such as for example nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as iron alloys, stainless steels, cobalt-chromium alloys, nitinol, and the like; and biologically derived materials such as bovine arteries/veins, pericardium and collagen. Stent components can also comprise bioresorbable organic materials such as poly(amino acids), poly(anhydrides), poly(caprolactones), poly(lactic/glycolic acid) polymers, poly(hydroxybutyrates) and poly(orthoesters). Any expandable stent component configuration which may be delivered to a treatment site is in accordance with the present disclosure.

In various embodiments, graft materials in stent-grafts may include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. Other embodiments for a graft member material can include high strength polymer fibers such as ultra-high molecular weight polyethylene fibers (e.g., Spectra®, Dyneema Purity®, etc.) or aramid fibers (e.g., Technora®, etc.). The graft member may include a bioactive agent. In one embodiment, an ePTFE graft includes a carbon component along a blood contacting surface thereof. Any graft member that may be delivered in a patient to a treatment site is in accordance with the present disclosure.

In various embodiments, a stent component and/or graft member may comprise a therapeutic coating. In these embodiments, the interior or exterior of the stent component and/or graft member can be coated with, for example, a CD34 antigen. Additionally, any number of drugs or therapeutic agents may be used to coat the graft member, including, for example heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, and thalidomide, among others.

In various embodiments, an expandable implant such as a stent-graft may be constrained by a restraining member or simply, a "sleeve" which circumferentially surrounds the expandable implant. In various embodiments, a sleeve circumferentially surrounds an expandable implant and constrains it in a collapsed configuration, in which the diameter is less than the diameter of the unconstrained implant. For example, a sleeve may constrain an expandable implant in a collapsed configuration for delivery within the vasculature.

In various embodiments, an expandable implant, such as a stent-graft, can be constrained by a plurality of sleeves, which together circumferentially surround the expandable implant. Each sleeve may be distinct and separate from the others, with each contributing to the restraining of only a portion of the expandable implant.

In various embodiments, a plurality of stents, grafts, and/or stent-grafts may be lined up longitudinally inside a single restraining sleeve.

In various embodiments, a plurality of stents, grafts, and/or stent-grafts may be lined up axially inside a plurality of axially aligned sleeves. In this case, adjacent sleeves may be tethered together.

In various embodiments, sleeves can be tubular and serve to constrain an expandable implant such as a stent-graft. In such configurations, sleeves are formed from a sheet of one or more materials wrapped or folded about the expandable implant. In the case where multiple sleeves are used to constrain an expandable implant, each sleeve can comprise at least one sleeve end adjacent to another sleeve end. While the illustrative embodiments herein are described as comprising one or more tubular sleeves, sleeves of any non-tubular shape that corresponds to an underlying expandable implant or that are otherwise appropriately shaped for a given application are also within the scope of the present disclosure.

In various embodiments, sleeves are formed by wrapping or folding the sheet of material(s) such that two opposing and/or parallel edges of the sheet are substantially aligned. Said alignment may or may not be parallel to or coaxial with the catheter shaft of a catheter assembly. In various embodiments, the edges of the sheet of material(s) do not contact each other.

In various embodiments, the edges of the sheet of material(s) do contact each other and are coupled with an elongated coupling member, as described below. In various other embodiments, the edges of the sheet of material(s) are aligned so that the edges of the same side of the sheet or sheets (e.g., the front or back of the sheet) are in contact with each other. In still other embodiments, the edges of opposite sides of the sheet of material(s) are in contact with each other, such that the edges overlap each other, such that a portion of one side of the sheet is in contact with a portion of the other side. Said another way, the front of the sheet may overlap the rear of the sheet, or vice versa.

In various embodiments, sleeves used to constrain expandable implants may further comprise radiopaque or echogenic markers. In such configurations, radiopaque markers may be located at the edges of sleeves, in the region where a coupling member is stitched through the series of openings. Radiopaque markers may assist in the positioning and orientation of the expandable implant within a vasculature, for example, by increasing the visibility through imaging of the location and orientation of elements such as sleeves coupling members, side branches, fenestrations, fenestratable areas, cuffs, anchors, and the like. As described in more detail below, since in accordance with the present disclosure imaging is not necessarily required during the multistage deployment of an implant, which can be followed by tactile indication transmitted to the clinician, imaging can be temporarily discontinued at certain points in the positioning or deployment procedures.

As used herein, "deployment" refers to the actuation of the medical device at the treatment site, such as for example, the removal of a sleeve on a self-expandable implant to allow the implant to expand. After such deployment, the sleeve or sleeves may be removed to allow the expandable implant to expand to its functional diameter and achieve the desired therapeutic outcome. In some embodiments, the sleeve or sleeves can remain implanted while not interfering with the expandable implant. In other embodiments, the sleeve or sleeves can be removed.

In various embodiments, deployment of a self-expandable stent-graft may comprise pulling out a coupling member that was used in securing the sleeve over the stent-graft, maintaining it in a collapsed configuration. This process of removing the coupling member from the sleeve is also referred to herein as "disengagement." Examples of restraining members and coupling members for releasably maintaining expandable devices in a collapsed state for endoluminal delivery can be found in U.S. Pat. No. 6,352,561 to Leopold et al., the content of which is incorporated herein by reference in its entirety.

In various embodiments, when the expandable implant such as a stent-graft is in position within the vasculature, the coupling member or members can be disengaged from the sleeve or sleeves from outside of the body of the patient, which allows the sleeve(s) to open and the expandable implant to expand. As discussed above, the expandable implant may be self-expanding, or the implant may be expanded by a device, such as a balloon. The coupling member or members may be disengaged from the sleeve or sleeves by a mechanical mechanism operated from outside of the body of the patient. For example, the member or members may be disengaged by applying sufficient tension to the member or members. In another example, a dial or rotational element may be attached to the coupling member or members outside of the body. Rotation of the dial or rotational element may provide sufficient tension to disengage the coupling member or members.

In various embodiments, this disengagement process may be stepwise, or in other words, in stages. The overall deployment of an expandable implant in accordance with the present disclosure may comprise a multistage or stepwise deployment of the implant. Such deployment may comprise the multistage or stepwise disengagement of a coupling member from one or more restraining sleeves. Each step or stage in the stepwise deployment of an expandable device may be referred to as partial deployment. In stepwise or multistage deployment of an expandable implant, it may be useful to expand only a portion of the expandable implant up to a particular point, such as for example a side branch fenestration, or in stages up to each of a plurality of particular points sequentially. Ideally, the clinician will know in real time when a partial deployment of the implant reaches the one or more fenestrations or other particular points that may be desirable.

In various embodiments, the present disclosure provides tactile indication of the progress of a multistage or stepwise disengagement procedure that can be sensed by the clinician performing such procedure. The tactile indication is provided by one or more tactile indictors located on the device as will be explained below.

In various embodiments of the present disclosure, the multistage deployment may stop at a desired point or at desired points corresponding to one or more target portions. A target portion for purposes of the present disclosure is the desired point between stages of partial deployment.

In various embodiments of the present disclosure, an expandable implant may comprise at least one target portion. In such configurations, the target portion or portions are located on the surface of the expandable implant. In various embodiments, the target portion or portions may comprise side branch fenestrations. Side branch fenestrations allow for branching devices, such as branching stent grafts, to be connected to and in with communication the expandable implant. In various configurations, the diameter of the side branch fenestrations may be approximately the same as the vessel to be repaired. In other configurations, the diameter of the side branch fenestrations may be larger than the diameter of the vessel to be repaired. In yet other configurations, the diameter of the side branch fenestrations may be less than the diameter of the vessel to be repaired.

In various embodiments, a target portion may comprise a drug eluting element. In these configurations, a drug eluting element comprises a segment which releases a therapeutic agent or drug once the target portion has been exposed to the vasculature of a patient. Examples of such therapeutic agents or drugs include prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione, erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-.beta.-estradiol, ethinyl estradiol, ethinyl estradiol 3-methyl ether, prednisolone, 17-.beta.-hydroxyprogesterone acetate, 19-nor-progesterone, norgestrel, norethindrone, norethisterone, norethiederone, progesterone, norgesterone, norethynodrel, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, atorvastatin, simvastatin, pravastatin, fluvastatin, lovastatin, cephalexin, erythromycin, haloperidol, zomepirac, ferrous lactate, vincamine, phenoxybenzamine, diltiazem, milrinone, captopril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

In various embodiments of the present disclosure, the target portions may comprise radiopaque segments. In such configurations, the target portions may be surrounded by radiopaque segments or markers which assist in locating and orienting the target portions and the expandable implant within the patient's vasculature. In various embodiments, the target portions comprise both radiopaque segments and either a side branch fenestration or a fenestratable portion. In these configurations, radiopaque segments may, among other things, assist in the delivery to and installation of side branch stent-grafts to the target portions.

Figure 1:
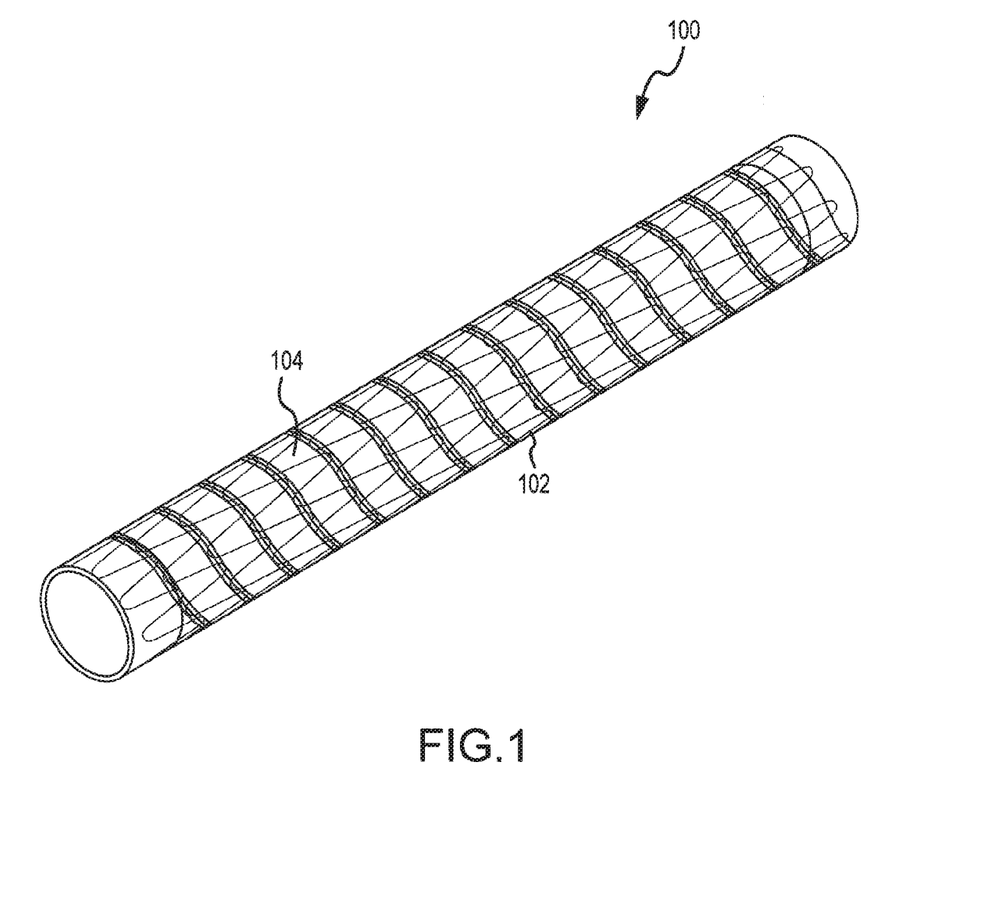
FIG. 1 illustrates a perspective view of an embodiment of an expanded medical device in a collapsed configuration in accordance with the present disclosure.

The above being noted, with reference now to FIG. 1, a medical device 100 in accordance with the present disclosure is illustrated. Medical device 100 comprises a stent 102 and a graft member 104. In various embodiments, graft member 104 is affixed to the outside surface of stent 102 such that once deployed, graft member 104 is placed into contact with a vessel wall. In other embodiments, graft member 104 is affixed to the inside surface of stent 102 such that once deployed, graft member 104 is not in contact with a vessel wall.

Figure 2:
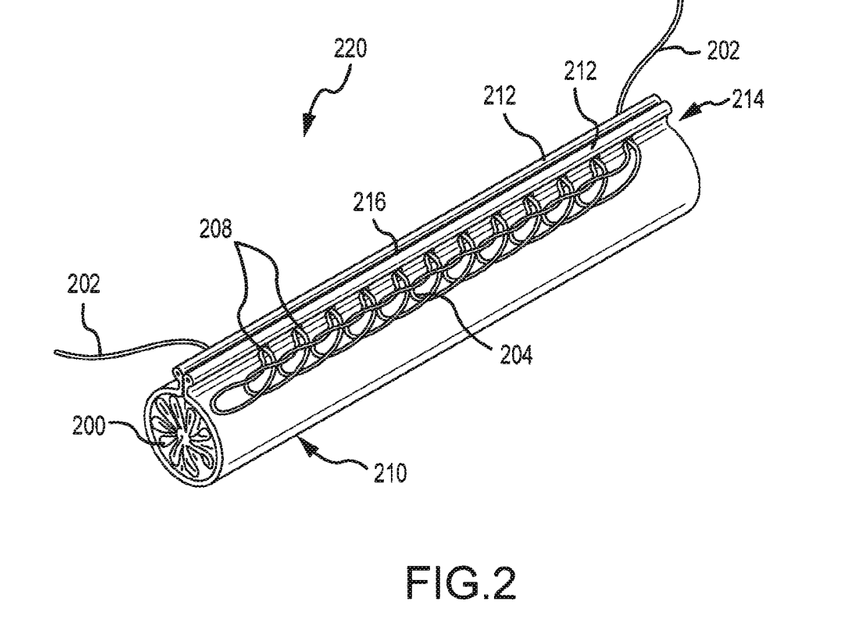
FIG. 2 illustrates a perspective view of an embodiment of an expandable medical device constrained in a collapsed configuration in accordance with the present disclosure.

Referring now to FIG. 2, an embodiment of a medical device assembly 220 in accordance with the present disclosure comprises an expandable device 200. The expandable device 200, such as a stent-graft, is compacted or constrained by a restraining member or sleeve 210 to an outer peripheral dimension suitable for endoluminal delivery of the device to a treatment site. In various embodiments, restraining members such as sleeve 210 may comprise materials similar to those used to form a graft member. For example, flattened, thin wall ePTFE tubing may be the precursor to make the sleeve.

In the embodiment illustrated, the sleeve 210 includes generally opposing and/or parallel edges 212 each with a plurality of openings 208 such as eyelets. The openings 208 are arranged linearly to form stitch lines 214 extending along the opposing edges 212 of the sleeve 210. The sleeve 210 extends around the device 200, with the opposing edges releasably secured together into a releasable seam 216 that runs axially along the length of the sleeve 210. In this case, a flat sheet of material may be wrapped circumferentially around the implant for closure to form such a seam.

In various embodiments, the releasable seam 216 may be held together by an elongated coupling member 202 extending through or woven through the openings 208. The threading or weave may comprise any variation of stitching, such as for example a chain stitch comprising individual slip knots or loops 204 that are interconnected. In various embodiments, the elongated coupling member 202 may comprise a woven fiber. In other embodiments, the coupling member 202 may comprise a monofilament fiber. Any type of string, cord, thread, fiber, or wire capable of maintaining a sleeve in a tubular shape is within the scope of the present disclosure. The coupling member 202 may comprise ePTFE fiber such as (KORETEK®), sutures of polyethers such as polyethylene terephthalate (DACRON® or MYLAR®) or polyacrylamides such as KEVLAR®. The coupling member 202 may alternatively comprise a metal wire made from nitinol, stainless steel, or gold. In various embodiments, the coupling member 202 may extend long enough to form a remote pull line or may be coupled to a separate pull line of the same or different material.

In various embodiments, when the expandable device is in position at the treatment site of the patient, the elongated coupling member or coupling members 202 can be disengaged from the sleeve or sleeves 210 from outside of the body of the patient, which allows the sleeve(s) to open and the expandable device 200 to expand. As mentioned above, this disengagement process may be stepwise, or in other words, in stages.

In various embodiments, the coupling member 202 can extend through a catheter shaft and be accessed by a clinician through proximal connectors. Tensioning, actuation and displacement of the coupling member 202 from the openings 208 allows the sleeve 210 to open along the releasable seam 216 and for the device 200 to expand from a compacted state, suitable for endoluminal delivery to a treatment site, toward a larger outer peripheral dimension during deployment at the treatment site. The tensioning and displacement of the coupling member 202 from the openings 208 can be felt by the clinician thereby providing a tactile sense of the opening of the sleeve 210 and deployment of the device 200, which otherwise may have required imaging.

Figure 3:
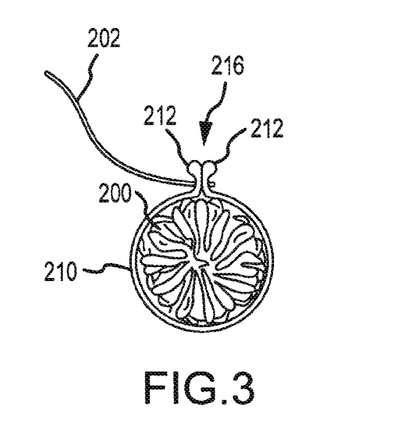
FIG. 3 illustrates a cross sectional view of an embodiment of an expandable medical device constrained in a collapsed configuration in accordance with the present disclosure.

Referring now to FIG. 3, an embodiment of an assembly in accordance with the present disclosure is illustrated in cross-section. As shown, the sleeve 210 is wrapped circumferentially around an expandable device 200 to restrain it in a compacted configuration. The sleeve 210 extends around the device 200, with the opposing edges 212 releasably secured together by coupling member 202 into a releasable seam 216 that runs axially along the length of the sleeve 210.

Figure 4:
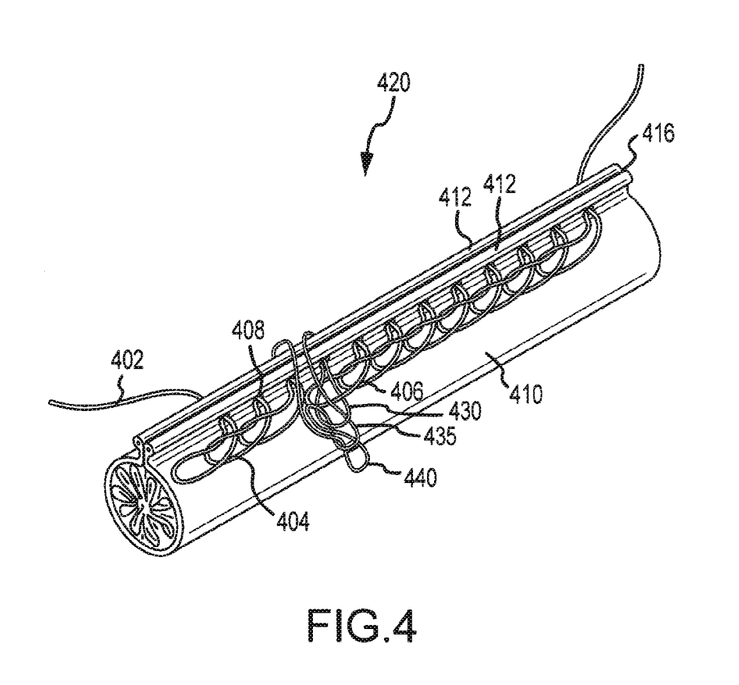
FIG. 4 illustrates a close-up perspective view of an embodiment of an expandable medical device comprising a tactile indicator in accordance with the present disclosure.

Referring now to FIG. 4, an embodiment of a tactile indicator in accordance with the present disclosure is configured on the assembly 420 to provide a change in the tension of the elongated coupling member 402 during disengagement, which can be sensed by the clinician. The assembly 420 comprises a sleeve 410 having opposing edges 412 stitched into a releasable seam 416 with a chain stitch of loops such as loop 404 through openings 408. This embodiment of one such tactile indicator comprises a slack loop section made up of the three separate slack loops 430, 435 and 440. Such a slack loop is formed by first pulling out a length of slack of thread-like coupling member 402 from each side of the releasable seam 416 during the sewing of the releasable seam 416. On the side of the assembly having the interlaced chain stitches 406, the pulled slack is placed through chain stitch 406 to create loop 430. Then, the pulled excess from the opposite side of the assembly is brought over the top of releasable seam 416 and tucked into loop 430 to form a second loop 435. Finally, the end of the same slack used to create loop 435 is tucked through loop 435 to form the third loop 440. In practice, the chain stitch may be much tighter than what is illustrated, where the illustration of general loose stitching helps to show the presence of a slack loop interrupting an otherwise uniformly tight chain stitch.

In various embodiments in accordance with the present disclosure, a tactile indicator may comprise a slip knot or other knotted structure in the coupling member that will produce an increase in tension at a certain point during disengagement from the sleeve. In various embodiments, the change in tension felt by the clinician may be either an increase or a decrease in tension, the choice made possible by how the tactile indicator is configured on the device, (for example, slip knot versus slack loop). In various embodiments, any number of tactile indicators may be configured on a medical device assembly in accordance with the present disclosure in order to provide any number and combination of increases and decreases in tension that can be felt by the clinician during disengagement of the coupling member.

In various embodiments in accordance with the present disclosure, a tactile indicator comprising a knotted structure in the elongated coupling member 402 may also be used to prevent premature unraveling of the elongated coupling member 402 and opening of the releasable seam 416. For example, a knotted structure in the elongated coupling member 402 at or near the proximal or distal end or both ends of a medical device assembly may be used to prevent premature or runaway deployment of an expandable device, such as may happen during insertion into, or delivery through, a body conduit. Once the device is known to be in position at the treatment site, the clinician may pull the knotted structure out by initially applying additional force to begin deployment. The drop in tension after the knotted structure is successfully pulled out provides tactile indication to the clinician that opening of the releasable seam 416 has begun.

Figure 5:
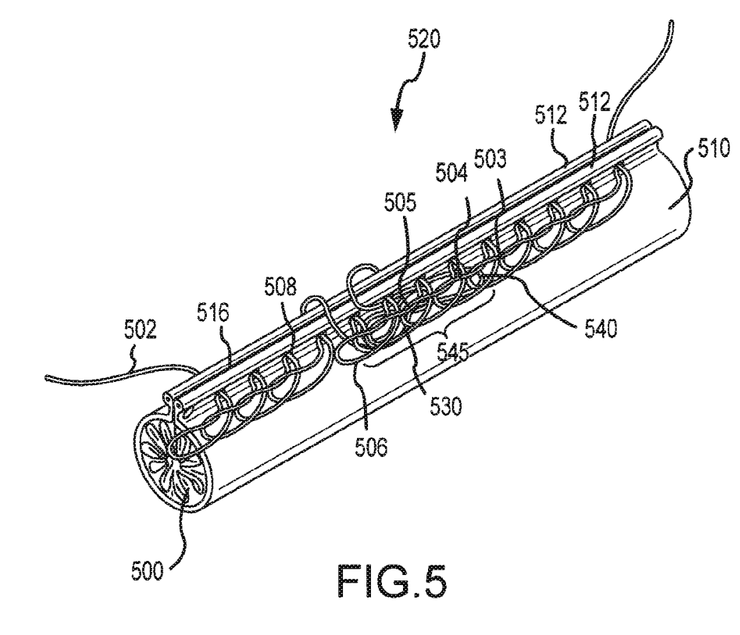
FIG. 5 illustrates a close-up perspective view of an embodiment of an expandable medical device comprising a tactile indicator in accordance with the present disclosure.

Referring now to the embodiment of FIG. 5, the assembly 520 comprises a tactile or stage indicator comprising a disengaged portion 545 characterized by a slack loop 530, 540 interweaved with several of the loops 505 through 503 of the elongated coupling member 502 along the stitch line of the interlocking chain stitch that secures opposing edges 512 together into releasable seam 516. This disengaged portion 545 is not releasably coupled to the sleeve 510, and as such, it will cause a relief in tension when reached during disengagement of the elongated coupling member 502 that can be felt by the clinician. As illustrated, the disengaged portion 545 is another embodiment of a tactile indicator according to the present disclosure. The disengaged portion 545 in the elongated coupling member 502 may be situated in proximity to a location on the sleeve 510 and/or device 500 where a point of partial deployment is desired and where it is important for the clinician to know when reached.

In various embodiments, the loops 530 and 540 are formed by pulling the sewn elongated coupling member 502 in the desired location to create loop 540, pulling a portion of loop 540 through the first chain stitch 506 to form loop 530, tucking the end of loop 540 through loop 530 and then releasably securing the loops 530 and 540 to eliminate any dangling by weaving the combination of loops 530 and 540 through other chain stitches such as 505, 504, 503 of the elongated coupling member 502. Other suitable means of releasably securing the slack can be utilized. By this arrangement, a partial length of the sleeve 510 can be opened, thereby resulting in a partial deployment of the device 500. During the deployment, as discussed above, the clinician can have a tactile feel of the device deploying as a result of displacement of the elongated coupling member 502 from the openings 508 in the sleeve 510. The tactile feel can be characterized as a catch and release sensation as the elongated coupling member 502 is displaced from successive openings 508 along the stitch line.

When the displacement of the coupling member 502 along releasable seam 516 reaches the slack loop 530, the tactile catch and release feeling yields to a feeling of slack or lack of resistance in the elongated coupling member 502 felt by the clinician which can indicate that a desired partial deployment point has been reached. The felt slack can, for example, be positioned to indicate that the device has been deployed up to, at or just after a particular feature of the device, such as a side branch opening or fenestratable portion or other similar feature, characteristic, or target portion of the device. In any case, once the slack loop 530 is reached during the first stage of actuation or displacement of the elongated coupling member 502 along releasable seam 516, the clinician will feel a change in tactile feel and can choose to stop deployment of the device 500 at this point, or continue on with a second or next phase of deployment until deployment is complete.

Figure 6:
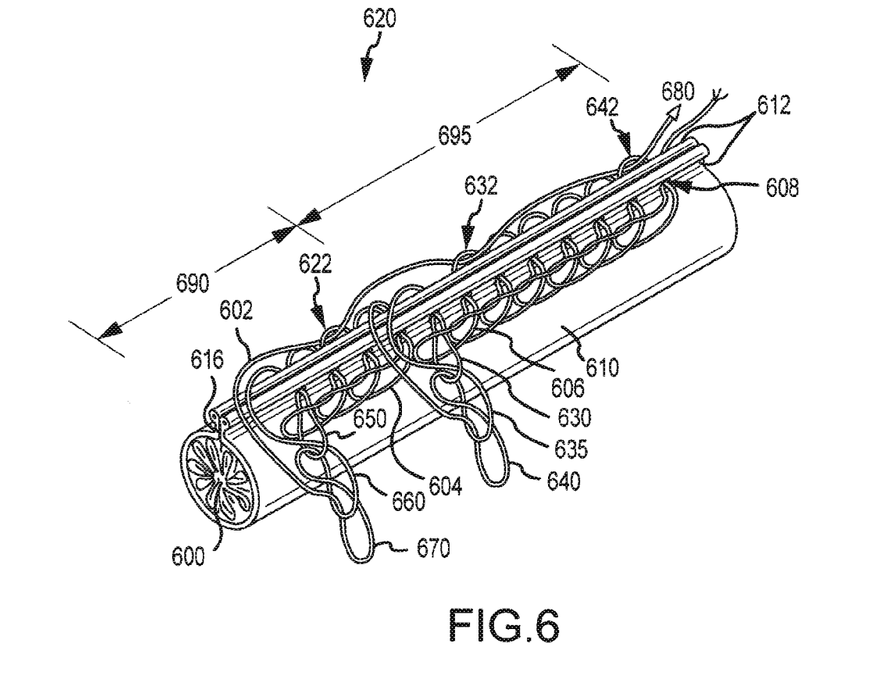
FIG. 6 illustrates a close-up perspective view of an embodiment of an expandable medical device comprising a tactile indicator in accordance with the present disclosure.

Referring now to the embodiment of FIG. 6, the assembly 620 comprises a tactile indicator further comprising the interlaced slack loops 630, 635 and 640 interwoven into the next adjacent chain stitch loop 606. The tactile indicator separates the assembly into a first stage of deployment 690 and second stage of deployment 695. At the distal end of the first stage of deployment 690, the elongated coupling member 602 is tucked into a series of loops 650, 660 and 670. The first stage of deployment of the constrained device 600 begins with a tensioning of the end of the elongated coupling member 680. A beginning tension or resistance will be sensed by the clinician as loop 670 is pulled from loop 660 and as loop 660 is pulled free from loop 650. After the initial loops are pulled through, sleeve 610 will begin to open across the releasable seam 616 with separation of the opposing edges 612 of the sleeve as the elongated coupling member 602 is pulled far enough out to begin pulling apart the chain stitches. As illustrated, the elongated coupling member running from the distal side to the proximal side of the device may be looped into the backside of any number of the chain stitches as indicated by 622, 632 and 642. The end of the first stage of deployment will be sensed by the clinician when the tactile indicator is reached. At this point, the interlaced loops 640 and 635 need to be pulled out sequentially before the second stage of deployment can begin with loop 630 being pulled out through the releasable seam 616. While loops 640 and 635 are being pulled out from loop 630, a change in tension in the elongated coupling member 602 will be sensed by the clinician, giving real time indication that the desired partial deployment location has been reached. At this point of partial deployment, the deployment may be stopped. To begin the second stage of deployment, the elongated coupling member 602 may be further pulled out of the assembly unlacing the second series of chain stitches. The clinician will again sense a change in tension on the elongated coupling member as the second series of chain stitches are unraveled.

In various embodiments, multiple secured loops of slack are provided at predetermined positions along the length of the elongated coupling member to allow for multiple stages of deployment. At the transition between each stage of deployment, the tactile indicator provides tactile feedback to the clinician such that the clinician will feel either an increase or decrease in tension as determined by the nature of the tactile indicator.

In various embodiments, a single elongated coupling member may be used to constrain the diameter of more than one sleeve arranged on a longitudinal axis, with a slack loop configured in the elongated coupling member at each point between adjacent sleeves. In this way, the clinician will feel when each sleeve is consecutively opened.

In various embodiments, the loop of slack can be arranged to increase or decrease deployment force with appropriate combinations of opening size, opening spacing, coupling member type, material and/or dimensions, weaving pattern, knots, biocompatible adhesives and/or coatings, or other factors contributing to the tactile feel of the actuation of the coupling member.

Figure 7:
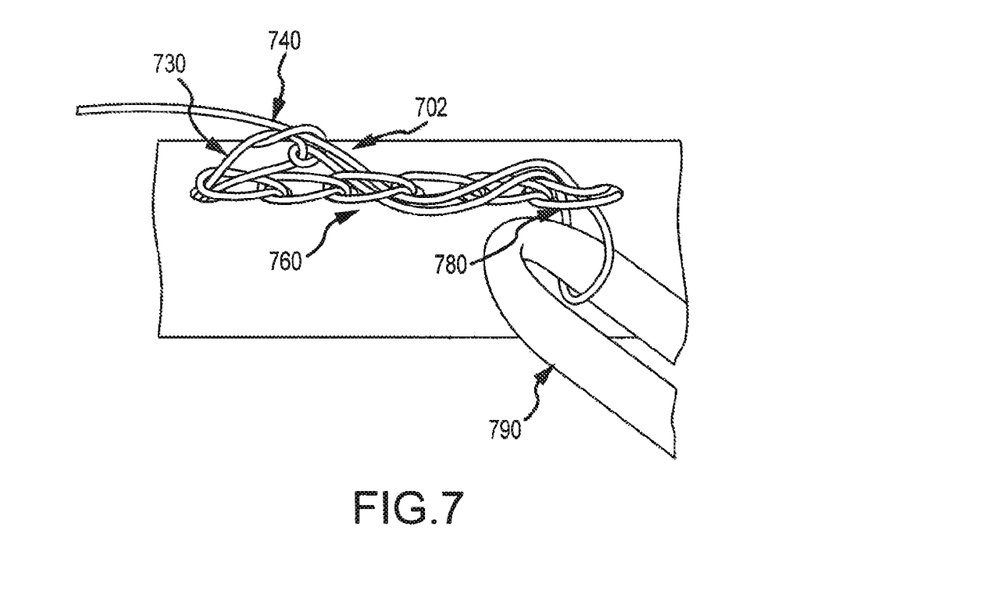
FIG. 7 illustrates a front view of an embodiment of a securing feature for a medical device assembly in accordance with the present disclosure.

Now referring to FIG. 7, an embodiment of a feature to secure the elongated coupling member 702 to a device is illustrated. The process for making such a configuration is to make two slip knots in the elongated coupling member 702 from the end of the loop while holding the last stitch. While keeping the knots fairly tight, a third loop is left to a length of at least about 4 cm. The elongated coupling member 702 is then looped under the third double stitch 760, which is away from the reinforcement line. Ensuring that the loop is pointing toward the fold, the lacing is repeated under the sixth double stitch 780. Lastly, elongated coupling member is secured with a lock clip as illustrated such that the elongated coupling member does not inadvertently begin to disengage.

Figure 8:
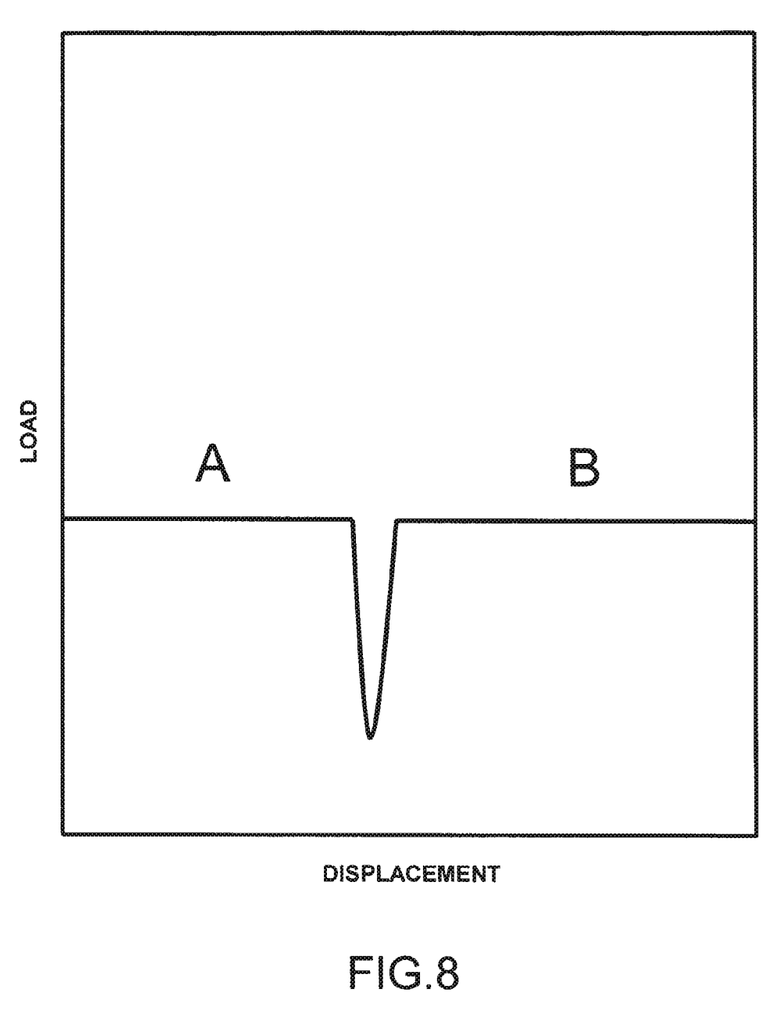
FIG. 8 illustrates force to displacement expected during deployment of an embodiment of a medical device in accordance with the present disclosure.

Referring now to FIG. 8, the change in the amount of force applied to the elongated coupling member versus the displacement of the elongated coupling member over the course of deployment for a medical device in accordance with the present disclosure may have the general features as illustrated. For example, a device comprising one tactile indicator divides deployment of the device into two stages of deployment, illustrated as "A" and "B" in the hypothetical plot. In this exemplary embodiment, the tactile indicator may comprise a slackened loop that provides a decrease in the amount of force applied to the elongated coupling member to pull out the slack. This decrease in tension illustrated in the hypothetical graph will be sensed by the clinician and will signal to the clinician that the device is between the two stages of deployment "A" and "B."

In the hypothetical plot of force versus displacement illustrated in FIG. 8, and in the plots that follow, various changes in tension may occur during deployment that are not illustrated. For example, there may be an increase in force at the very beginning of deployment, such as required to disengage a starting slip knot. There may also be repetitive peaks and valleys appearing like "noise" in the force throughout most of the deployment resulting from the force required to pull out each individual chain stitch in the elongated coupling member. Also, the increase or decrease in tension at each tactile indicator may comprise multiple changes in tension. For example, multiple slackened loops interwoven into a chain stitch may result in a more "saw tooth" pattern in the force versus displacement rather than just a single peak for the tactile feedback. As each slackened loop in the same tactile indicator is reached and pulled out, the changes in tension may result in more of a saw tooth shaped peak rather than a smooth peak as illustrated. In various embodiments, the overall tension in the elongated coupling member over the course of deployment may trend downwards or upwards, or may have no discernible trend at all. In various embodiments, the tension may drop more sharply and trail off as the elongated coupling member is entirely freed from the constraining sleeve and removed from the patient.

Figure 9:
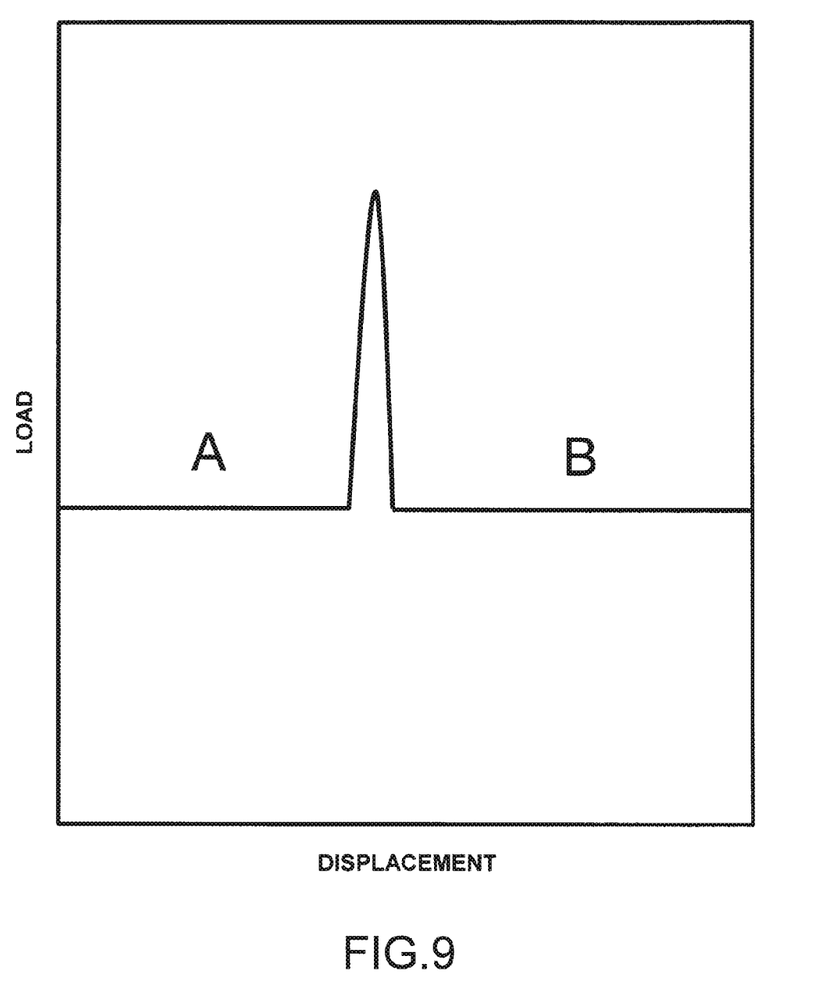
FIG. 9 illustrates force to displacement expected during deployment of an embodiment of a medical device in accordance with the present disclosure.

Referring now to FIG. 9, the change in force applied to an elongated coupling member during the course of deployment versus the displacement of the elongated coupling member may have the general features as illustrated. For example, a device in accordance with the present disclosure may comprise a single tactile indicator dividing the deployment of the device into two stages, "A" and "B" as illustrated. In various embodiments, the use of a slip knot or other knotted structure can provide an increase in tension between stages of deployment. In the hypothetical plot of FIG. 9, a rise in the force required to displace the elongated coupling member is indicative of the force required to pull out the knotted structure in the elongated coupling member. This increase in tension can be sensed by the clinician, and it provides an indication to the clinician that the deployment procedure is at the transition between the two stages.

Figure 10:
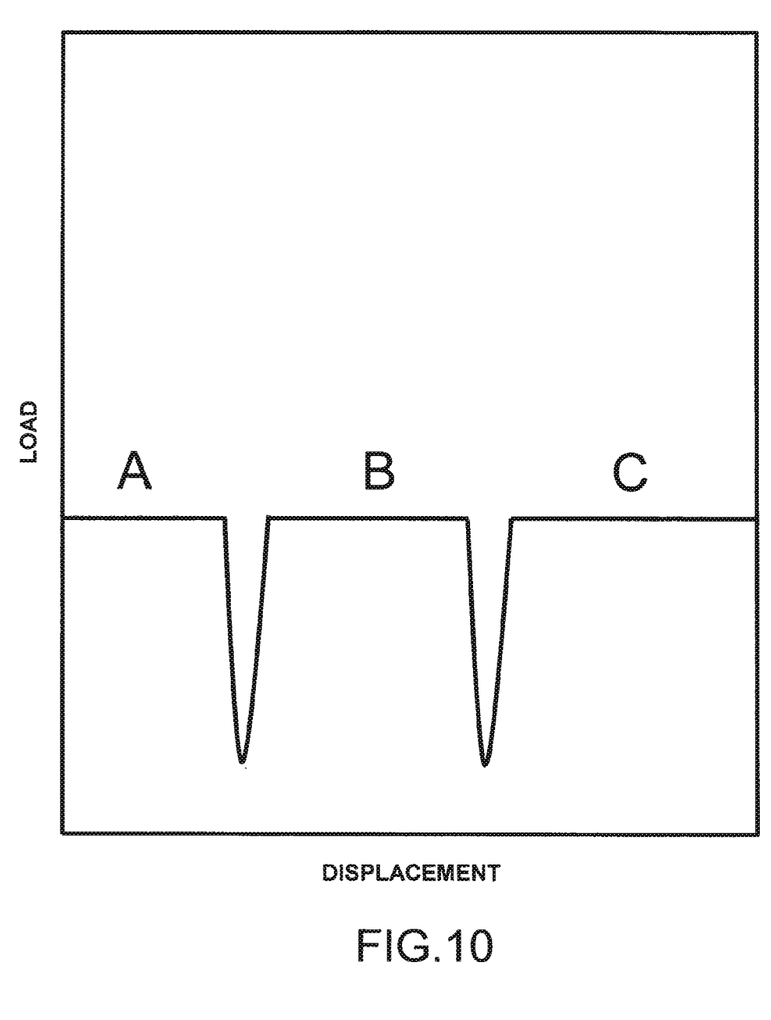
FIG. 10 illustrates force to displacement expected during deployment of an embodiment of a medical device in accordance with the present disclosure.

FIG. 10 illustrates a hypothetical force versus displacement plot expected during deployment of an embodiment of a device in accordance with the present disclosure having two tactile indicators, each producing decreases in tension in the elongated coupling member when reached. In this embodiment, two tactile indicators divide deployment of the device into three stages of deployment, "A," "B" and "C" as illustrated.

Figure 11:
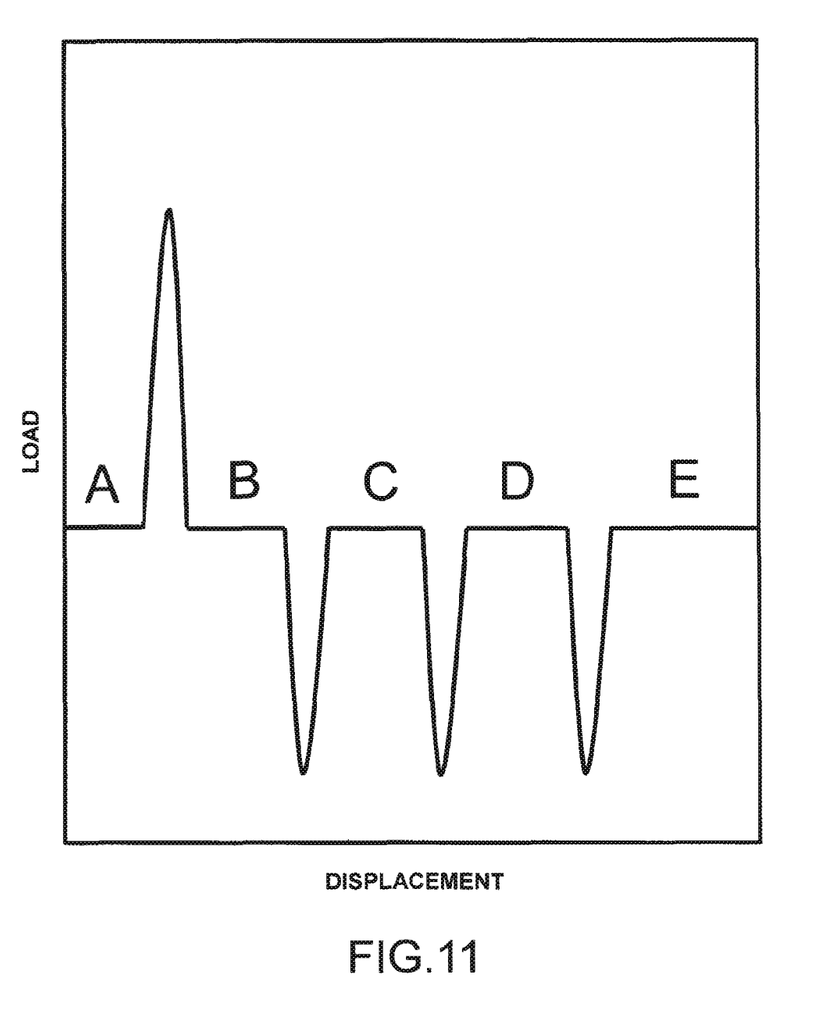
FIG. 11 illustrates force to displacement expected during deployment of an embodiment of a medical device in accordance with the present disclosure.

FIG. 11 illustrates the expected force versus deployment for a device comprises a plurality of tactile indicators dividing the deployment into five stages, "A," "B," "C," "D," and "E." As discussed above, various embodiments of the device may include any number of tactile indicators, with any of the indicators configured to provide an increase or decrease in tension during displacement of the elongated coupling member sensed by the clinician. In this exemplary embodiment, the first tactile indicator reached during deployment provides an increase in tension sensed by the clinician. The rise in tension signals to the clinician that the transition between stages "A" and "B" has been reached. In this example, the remaining tactile indicators provide decreases in tension sensed by the clinician. As each decrease in tension is transmitted, the clinician is prompted that a transition between stages of deployment has been reached. In various embodiments, a device may include any number and any combination of tactile indicators that provide increases and/or decreases in tension sensed by the clinician as the device is deployed.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. An assembly comprising: an expandable device; a restraining member wrapped circumferentially around the expandable device and having opposing edges, the restraining member having a proximal end and a distal end; an elongated coupling member configured to form a releasable seam axially along a length of the restraining member and being configured to releasably secure together the opposing edges of the restraining member, the elongated coupling member being configured to release the releasable seam in response to tension applied thereto; and a plurality of tactile indicators formed by portions of the elongated coupling member and located at a plurality of locations along the releasable seam, and one of the plurality of tactile indicators comprising a knotted structure arranged near at least one of the distal end of the restraining member and the proximal end of the restraining member configured to initiate a first stage of deployment and configured to transmit an increase in tension, and another of the plurality of tactile indicators comprises a slack loop section interwoven with the elongated coupling member arranged at and configured to initiate a second stage of deployment that transmits a decrease in tension in response to the tension applied to the coupling member, wherein at least one of the plurality of tactile indicators is located at a desired point of partial deployment of the expandable device and the first stage of deployment occurs prior to the second stage of deployment.

2. The assembly of claim 1, wherein said device comprises an endoluminal prosthesis.

3. The assembly of claim 1, wherein said device is at least one of a graft, a stent, or a stent-graft.

4. The assembly of claim 1, wherein said device is self-expandable.

5. The assembly of claim 1, wherein said device is balloon expandable.

6. The assembly of claim 1, comprising more than one expandable device.

7. The assembly of claim 1, comprising more than one restraining member.

8. The assembly of claim 7, wherein the at least one tactile indicator is located on the assembly between any two adjacent restraining members.

9. The assembly of claim 1, wherein said partial deployment comprises a target portion.

10. The assembly of claim 9, wherein said target portion comprises a side branch fenestration on a surface of said device.

11. The assembly of claim 1, wherein said releasable seam includes a chain stitch of loops extending through opening formed along said opposing edges of said retraining member.

12. The assembly of claim 11, wherein said slack loop extends through one of the loops of said chain stitch.

13. The assembly as set forth in claim 12, wherein a second slack loop extends through said slack loop.

14. The assembly as set forth in claim 13, wherein a third slack loop extends through the second slack loop.

15. The assembly as set forth in claim 14, wherein said first, second and third length loops are formed from a same length of slack along said elongated coupling member.

16. A method for partially deploying a device in a patient comprising: positioning an assembly in the patient, said assembly comprising: an expandable device; a restraining member wrapped around the device and having opposing edges and having a proximal end and a distal end; an elongated coupling member forming a releasable seam axially along a length of the restraining member and being configured to releasably secure together the opposing edges of the restraining member, and a plurality of tactile indicators formed by portions of the elongated coupling member and located at a plurality of locations along the releasable seam of the elongated coupling member, wherein at least one of the plurality of tactile indicators comprises a knotted structure arranged near at least one of the distal end of the restraining member and the proximal end of the restraining member and another of the plurality of tactile indicators comprises a slack loop section interwoven with the elongated coupling member initiating a first stage of deployment and partially releasing the restraining member and the knotted structure by tensioning and displacing the elongated coupling member from a position outside the patient thereby indicating an increase in tension; and initiating a second stage of deployment and partially releasing the restraining member and the slack loop section by tensioning and displacing the elongated coupling member from the position outside the patient thereby indicating a decrease in tension, the first stage of deployment occurs prior to the second stage of deployment.

17. The method of claim 16, further comprising sensing a lack of resistance in said elongated coupling member which coincides with reaching a slack loop in said elongated coupling member during displacement.

18. The method of claim 17, wherein the sensing of a lack of resistance during said partial deployment is felt by a clinician performing the partial deployment of said device.

19. The method of claim 16, wherein said device is at least one of a graft, a stent, or a stent-graft.

20. The method of claim 16, wherein said device is self-expandable.

21. The method of claim 16, wherein said partial deployment comprises a target portion on said device.

22. The method of claim 21, wherein said target portion comprises a side branch fenestration on a surface of said device.

* * * * *